United States Patent
Sherman et al.

(12)

(10) Patent No.: US 6,274,171 B1
(45) Date of Patent: Aug. 14, 2001

(54) EXTENDED RELEASE FORMULATION OF VENLAFAXINE HYDROCHLORIDE

(75) Inventors: Deborah M. Sherman, Plattsburgh; John C. Clark, Peru, both of NY (US); John U. Lamer, St. Albans, VT (US); Steven A. White, Champlain, NY (US)

(73) Assignee: American Home Products Corporation, Madison, NJ (US)

( * ) Notice: Subject to any disclaimer, the term of this patent is extended or adjusted under 35 U.S.C. 154(b) by 0 days.

(21) Appl. No.: 09/488,629

(22) Filed: Jan. 20, 2000

Related U.S. Application Data

(63) Continuation-in-part of application No. 08/964,328, filed on Nov. 5, 1997, now abandoned, which is a continuation-in-part of application No. 08/821,137, filed on Mar. 20, 1997, now abandoned.

(60) Provisional application No. 60/014,006, filed on Mar. 25, 1996.

(51) Int. Cl.[7] ............................. A61K 9/52; A61K 9/54; A61K 9/62
(52) U.S. Cl. ................ 424/461; 424/457; 424/458; 424/459; 514/781; 514/962
(58) Field of Search ..................... 424/495, 494, 424/461, 458, 459, 457, 456, 462

(56) References Cited

U.S. PATENT DOCUMENTS

| | | | |
|---|---|---|---|
| 3,954,959 | 5/1976 | Pedersen | 424/21 |
| 4,138,475 * | 2/1979 | McAinsh et al. | 424/19 |
| 4,369,172 | 1/1983 | Schor et al. | 424/19 |
| 4,389,393 | 6/1983 | Schor et al. | 424/19 |
| 4,535,186 | 8/1985 | Husbands et al. | 564/336 |
| 4,966,768 | 10/1990 | Michelucci et al. | 424/468 |
| 5,506,270 | 4/1996 | Upton et al. | 514/730 |
| 5,552,429 * | 9/1996 | Wong et al. | 514/415 |

FOREIGN PATENT DOCUMENTS

| | | |
|---|---|---|
| 0654264 | 11/1994 | (EP) . |
| 0667150 | 1/1995 | (EP) . |
| 0797991 | 10/1997 | (EP) . |
| 9427589 | 12/1994 | (WO) . |
| 9737640 | 10/1997 | (WO) . |

* cited by examiner

*Primary Examiner*—James M. Spear
(74) *Attorney, Agent, or Firm*—Rebecca R. Barrett

(57) ABSTRACT

This invention relates to a 24 hour extended release dosage formulation and unit dosage form thereof of venlafaxine hydrochloride, an antidepressant, which provides better control of blood plasma levels than conventional tablet formulations which must be administered two or more times a day and further provides a lower incidence of nausea and vomiting than the conventional tablets. More particularly, the invention comprises an extended release formulation of venlafaxine hydrochloride comprising a therapeutically effective amount of venlafaxine hydrochloride in spheroids comprised of venlafaxine hydrochloride, microcrystalline cellulose and, optionally, hydroxypropylmethylcellulose coated with a mixture of ethyl cellulose and hydroxypropylmethylcellulose.

25 Claims, No Drawings

US 6,274,171 B1

EXTENDED RELEASE FORMULATION OF VENLAFAXINE HYDROCHLORIDE

This application continuation-in-part of Application Ser. No. 08/964,328, filed Nov. 5, 1997 abandoned, which is a continuation-in-part of Application Ser. No. 08/821,137, filed Mar. 20, 1997 abandoned, which, in turn, claims priority from Provisional Application No. 60/014,006 filed Mar. 25, 1996.

BACKGROUND OF THE INVENTION

Extended release drug formulations are conventionally produced as compressed tablets by hydrogel tablet technology. To produce these sustained release tablet drug dosage forms, the active ingredient is conventionally compounded with cellulose ethers such as methyl cellulose, ethyl cellulose or hydroxypropylmethylcellulose with or without other excipients and the resulting mixture is pressed into tablets. When the tablets are orally administered, the cellulose ethers in the tablets swell upon hydration from moisture in the digestive system, thereby limiting exposure of the active ingredient to moisture. As the cellulose ethers are gradually leached away by moisture, water more deeply penetrates the gel matrix and the active ingredient slowly dissolves and diffuses through the gel, making it available for absorption by the body. An example of such a sustained release dosage form of the analgesic/anti-inflammatory drug etodolac (Lodine®) appears in U.S. Pat. No. 4,966,768. U.S. Pat. No. 4,389,393 discloses sustained release therapeutic compressed solid unit dose forms of an active ingredient plus a carrier base comprised of a high molecular weight hydroxypropylmethylcellulose, methyl cellulose, sodium carboxymethylcellulose and or other cellulose ether.

Where the production of tablets is not feasible, it is conventional in the drug industry to prepare encapsulated drug formulations which provide extended or sustained release properties. In this situation, the extended release capsule dosage forms may be formulated by mixing the drug with one or more binding agents to form a uniform mixture which is then moistened with water or a solvent such as ethanol to form an extrudable plastic mass from which small diameter, typically 1 mm, cylinders of drug/matrix are extruded, broken into appropriate lengths and transformed into spheroids using standard spheronization equipment. The spheroids, after drying, may then be film-coated to retard dissolution. The film-coated spheroids may then be placed in pharmaceutically acceptable capsules, such as starch or gelatin capsules, in the quantity needed to obtain the desired therapeutic effect. Spheroids releasing the drug at different rates may be combined in a capsule to obtain desired release rates and blood levels. U.S. Pat. No. 4,138,475 discloses a sustained release pharmaceutical composition consisting of a hard gelatin capsule filled with film-coated spheroids comprised of propanolol in admixture with microcrystalline cellulose wherein the film coating is composed of ethyl cellulose, optionally, with hydroxypropylmethylcellulose and/or a plasticizer.

Venlafaxine, 1-[2-dimethylamino)-1-(4-methoxyphenyl) ethyl]cyclohexanol, is an important drug in the neuropharmacological arsenal used for treatment of depression. Venlafaxine and the acid addition salts thereof are disclosed in U.S. Pat. No. 4,535,186. Venlafaxine hydrochloride is presently administered to adults in compressed tablet form in doses ranging from 75 to 350 mg/day, in divided doses two or three times a day. In therapeutic dosing with venlafaxine hydrochloride tablets, rapid dissolution results in a rapid increase in blood plasma levels of the active compound shortly after administration followed by a decrease in blood plasma levels over several hours as the active compound is eliminated or metabolized, until subtherapeutic plasma levels are approached after about twelve hours following administration, thus requiring additional dosing with the drug. With the plural daily dosing regimen, the most common side effect is nausea, experienced by about forty five percent of patients under treatment with venlafaxine hydrochloride. Vomiting also occurs in about seventeen percent of the patients.

BRIEF DESCRIPTION OF THE INVENTION

In accordance with this invention, there is provided an extended release (ER), encapsulated formulation containing venlafaxine hydrochloride as the active drug s component, which provides in a single dose, a therapeutic blood serum level over a twenty four hour period.

Through administration of the venlafaxine formulation of this invention, there is provided a method for obtaining a flattened drug plasma concentration to time profile, thereby affording a tighter plasma therapeutic range control than can be obtained with multiple daily dosing. In other words, this invention provides a method for eliminating the sharp peaks and troughs (hills and valleys) in blood plasma drug levels induced by multiple daily dosing with conventional immediate release venlafaxine hydrochloride tablets. In essence, the plasma levels of venlafaxine Is hydrochloride rise, after administration of the extended release formulations of this invention, for between about five to about eight hours (optimally about six hours) and then begin to fall through a protracted, substantially linear decrease from the peak plasma level for the remainder of the twenty four hour period, maintaining at least a threshold therapeutic level of the drug during the entire twenty-four period. In contrast, the conventional immediate release venlafaxine hydrochloride tablets give peak blood plasma levels in 2 to 4 hours. Hence, in accordance with the use aspect of this invention, there is provided a method for moderating the plural blood plasma peaks and valleys attending the pharmacokinetic utilization of multiple daily tablet dosing with venlafaxine hydrochloride which comprises administering to a patient in need of treatment with venlafaxine hydrochloride, a one-a-day, extended release formulation of venlafaxine hydrochloride.

The use of the one-a-day venlafaxine hydrochloride formulations of this invention reduces by adaptation, the level of nausea and incidence of emesis that attend the administration of multiple daily dosing. In clinical trials of venlafaxine hydrochloride ER, the probability of developing nausea in the course of the trials was greatly reduced after the first week. Venlafaxine ER showed a statistically significant improvement over conventional venlafaxine hydrochloride tablets in two eight-week and one 12 week clinical studies. Thus, in accordance with this use aspect of the invention there is provided a method for reducing the level of nausea and incidence of emesis attending the administration of venlafaxine hydrochloride which comprises dosing a patient in need of treatment with venlafaxine hydrochloride with an extended release formulation of venlafaxine hydrochloride once a day in a therapeutically effective amount.

The formulations of this invention comprise an extended release formulation of venlafaxine hydrochloride comprising a therapeutically effective amount of venlafaxine hydrochloride in spheroids comprised of venlafaxine hydrochloride, microcrystalline cellulose and, optionally, hydroxypropylmethylcellulose coated with a mixture of ethyl cellulose and hydroxypropylmethylcellulose. Unless otherwise noted, the percentage compositions mentioned herein refer to percentages of the total weight of the final composition or formulation.

More particularly, the extended release formulations of this invention are those above wherein the spheroids are comprised of from about 6% to about 40% venlafaxine hydrochloride by weight, about 50% to about 95% microcrystalline cellulose, NF, by weight, and, optionally, from about 0.25% to about 1% by weight of hydroxypropylmethylcellulose, USP, and coated with from about 2% to about 12% of total weight of film coating comprised of from about 80% to about 90% by weight of film coating of ethyl cellulose, NF, and from about 10% to about 20% by weight of film coating of hydroxypropylmethylcellulose, USP.

A preferred embodiment of this invention are formulations wherein the spheroids are comprised of about 30% to about 40% venlafaxine hydrochloride by weight, about 50% to about 70% microcrystalline cellulose, NF, by weight, and, optionally, from about 0.25% to about 1% by weight of hydroxypropylmethylcellulose, USP, and coated with from about 2% to about 12% of total weight of film coating comprised of from about 80% to about 90% by weight of film coating of ethyl cellulose, NF, and from about 10% to about 20% by weight of film coating of hydroxypropylmethylcellulose, USP.

Another preferred lower dose formulation of this invention are those wherein the spheroids are comprised less than 30% venlafaxine hydrochloride. These formulations comprise spheroids of from about 6% to about 30% venlafaxine hydrochloride by weight, about 70% to about 94% microcrystalline cellulose, NF, by weight, and, optionally, from about 0.25% to about 1% by weight of hydroxypropylmethylcellulose, USP, and coated with from about 2% to about 12% of total weight of film coating comprised of from about 80% to about 90% by weight of film coating of ethyl cellulose, NF, and from about 10% to about 20% by weight of film coating of hydroxypropylmethylcellulose, USP.

Within this subgroup of lower dose formulations are formulations in which the spheroids are comprised of from about 6% to about 25% venlafaxine hydrochloride and from about 94% to about 75% microcrystalline cellulose, with an optional amount of from 0.25% to about 1% by weight of hydroxypropylmethylcellulose. Another preferred subgroup of spheroids in these formulations comprises from about 6% to about 25% venlafaxine hydrochloride and from about 94% to about 75% microcrystalline cellulose, with an optional amount of from 0.25% to about 1% by weight of hydroxypropylmethylcellulose. A further preferred subgroup of spheroids in these formulations comprises from about 6% to about 20% venlafaxine hydrochloride and from about 94% to about 80% microcrystalline cellulose, with an optional amount of from 0.25% to about 1% by weight of hydroxypropylmethylcellulose. Within each of these subgroups is understood to be formulations in which the spheroids are comprised of venlafaxine HCl and microcrystalline cellulose in the amounts indicated, with no hydroxypropylmethylcellulose present. Each of these formulations is also preferably contained in a gelatin capsule, preferably a hard gelatin capsule.

DETAILED DESCRIPTION OF THE INVENTION

1-[2-(dimethylamino)-1-(4-methoxyphenyl)ethyl] cyclohexanol hydrochloride is polymorphic. Of the forms isolated and characterized to date, Form I is considered to be the kinetic product of crystallization which can be converted to Form II upon heating in the crystallization solvent. Forms I and II cannot be distinguished by their melting points but do exhibit some differences in their infrared spectra and X-ray diffraction patterns. Any of the polymorphic forms such as Form I or Form II may be used in the formulations of the present invention.

The extended release formulations of this invention are comprised of 1-[2-(dimethylamino)-1-(4-methoxyphenyl) ethyl]cyclohexanol hydrochloride in admixture with microcrystalline cellulose and hydroxypropylmethylcellulose. Formed as beads or spheroids, the drug containing formulation is coated with a mixture of ethyl cellulose and hydroxypropylmethyl cellulose to provide the desired level of coating, generally from about two to about twelve percent on a weight/weight basis of final product or more preferably from about five to about ten percent (w/w), with best results obtained at from about 6 to about 8 percent (w/w). More specifically, the extended release spheroid formulations of this invention comprise from about 30 to 40 percent venlafaxine hydrochloride, from about 50 to about 70 percent microcrystalline cellulose, NF, from about 0.25 to about I percent hydroxypropylmethylcellulose, USP, and from about 5 to about 10 percent film coating, all on a weight/weight basis. And preferably, the spheroid formulations contain about 35 percent venlafaxine hydrochloride, about 55 to 60 percent microcrystalline cellulose NF (Avicel® PH101), about one half percent hydroxypropylmethylcellulose 2208 USP (K3, Dow, which has a viscosity of 3 cps for 2% aqueous solutions, a methoxy content of 19–24% and a hydroxypropoxy content of 4–13%), and from about 6 to 8 percent film coating.

The film coating is comprised of 80 to 90 percent of ethyl cellulose, NF and 10 to 20 percent hydroxypropylmethylcellulose (2910), USP on a weight/weight basis. Preferably the ethyl cellulose has a ethoxy content of 44.0–51% and a viscosity of 50 cps for a 5% aqueous solution and the hydroxypropylmethylcellulose is USP 2910 having a viscosity of 6 cps at 2% aqueous solution with a methoxy content of 28–30% and a hydroxypropoxy content of 7–12%. The ethyl cellulose used herein is Aqualon HG 2834.

Other equivalents of the hydroxypropylmethylcelluloses 2208 and 2910 USP and ethyl cellulose, NF, having the same chemical and physical characteristics as the proprietary products named above may be substituted in the formulation without changing the inventive concept. Important characteristics of suitable hydroxypropylmethylcelluloses include a low viscosity, preferably less than 10 cps and more preferably 2–5 cps, and a gel temperature above that of the temperature of the extrudate during extrusion. As explained below, these and other characteristics which enable the extrudate to remain moist and soft (pliable) are preferred for the hydroxypropylmethylcellulose. In the examples below, the extrudate temperature was generally 50–55° C.

It was completely unexpected that an extended release formulation containing venlafaxine hydrochloride could be obtained because the hydrochloride of venlafaxine proved to be extremely water soluble. Numerous attempts to produce extended release tablets by hydrogel technology proved to be fruitless because the compressed tablets were either physically unstable (poor compressibility or capping problems) or dissolved too rapidly in dissolution studies. Typically, the tablets prepared as hydrogel sustained release formulations gave 40–50% dissolution at 2 hrs, 60–70% dissolution at 4 hrs and 85–100% dissolution at 8 hrs.

Numerous spheroid formulations were prepared using different grades of microcrystalline cellulose and hydroxypropylmethylcellulose, different ratios of venlafaxine hydrochloride and filler, different binders such as polyvinylpyrrolidone, methylcellulose, water, and polyethylene glycol of different molecular weight ranges in order to find a formulation which would provide a suitable granulation mix which could be extruded properly. In the extrusion process, heat buildup occurred which dried out the extrudate so much that it was difficult to convert the extruded cylinders into spheroids. Addition of hydroxypropylmethylcellulose 2208 to the venlafaxine hydrochloride-microcrystalline cellulose mix made production of spheroids practical.

The encapsulated formulations of this invention may be produced in a uniform dosage for a specified dissolution profile upon oral administration by techniques understood in the art. For instance, the spheroid components may be blended for uniformity with a desired concentration of active ingredient, then spheronized and dried. The resulting spheroids can then be sifted through a mesh of appropriate pore size to obtain a spheroid batch of uniform and prescribed size.

The resulting spheroids can be coated and resifted to remove any agglomerates produced in the coating steps. During the coating process samples of the coated spheroids may be tested for their distribution profile. If the dissolution occurs too rapidly, additional coating may be applied until the spheroids present a desired dissolution rate.

The following examples are presented to illustrate applicant's solution to the problem of preparation of the extended release drug containing formulations of this invention.

EXAMPLE NO. 1

Venlafaxine Hydrochloride Extended Release Capsules

A mixture of 44.8 parts ( 88.4% free base) of venlafaxine hydrochloride, 74.6 parts of the microcrystalline cellulose, NF, and 0.60 parts of hydroxypropylmethyl cellulose 2208, USP, are blended with the addition of 41.0 parts water. The plastic mass of material is extruded, spheronized and dried to provide uncoated drug containing spheroids.

Stir 38.25 parts of ethyl cellulose, NF, HG2834 and 6.75 parts of hydroxypropylmethylcellulose 2910, USP in a 1:1 v/v mixture of methylene chloride and anhydrous methanol until solution of the film coating material is complete.

To a fluidized bed of the uncoated spheroids is applied 0.667 parts of coating solution per part of uncoated spheroids to obtain extended release, film coated spheroids having a coating level of 3%.

The spheroids are sieved to retain the coated spheroids of a particle size between 0.85 mm to 1.76 mm diameter. These selected film coated spheroids are filled into pharmaceutically acceptable capsules conventionally, such as starch or gelatin capsules.

EXAMPLE NO. 2

Same as for Example 1 except that 1.11 parts of the film coating solution per part of uncoated spheroids is applied to obtain a coating level of 5%.

EXAMPLE NO. 3

Same as for Example 1 except that 1.33 parts of the film coating solution is applied to 1 part of uncoated spheroids to obtain a coating level of 6%.

EXAMPLE NO. 4

Same as for Example 1 except that 1.55 parts of the film coating solution is applied to 1 part of uncoated spheroids to obtain a coating level of 7%.

In the foregoing failed experiments and in Examples 1–4, the extrusion was carried out on an Alexanderwerk extruder. Subsequent experiments carried out on Hutt and Nica extruders surprisingly demonstrated that acceptable, and even improved, spheroids could be made without the use of an hydroxypropylmethylcellulose.

In such further experiments the applicability of the invention was extended to formulations wherein the weight percentage of venlafaxine hydrochloride is 6% to 40%, preferably 8% to 35%. Thus, the extended release spheroid formulations of this invention comprise from 6 to about 40 percent venlafaxine hydrochloride, from about 50 to about 94 percent microcrystalline cellulose, NF, optionally, from about 0.25 to about 1 percent hydroxypropylmethylcellulose, and from about 2 to about 12 percent, preferably about 3 to 9 percent, film coating.

Spheroids of the invention were produced having 8.25% (w/w) venlafaxine hydrochloride and the remainder (91.75%, w/w) being microcrystalline cellulose, with a coating of from 3 to 5% (w/w), preferably 4%, of the total weight. The spheroids with 8.25% venlafaxine hydrochloride and 4% coating were filled into No. 2 white opaque shells with a target fill weight of 236 mg.

Further spheroids of the invention were produced having 16.5% (w/w) venlafaxine hydrochloride and the remainder (83.5%,w/w) being microcrystalline cellulose, with a coating of from 4 to 6% (w/w), preferably 5%, of the total weight. The spheroids 16.5% venlafaxine hydrochloride and 5% coating were filled into No. 2 white opaque shells with a target fill weight of 122 mg.

The test for acceptability of the coating level is determined by analysis of the dissolution rate of the finished coated spheroids prior the encapsulation. The dissolution procedure followed uses USP Apparatus 1 (basket) at 100 rpm in purified water at 37° C.

Conformance with the dissolution rate given in Table 1 provides the twenty-four hour therapeutic blood levels for the drug component of the extended release capsules of this invention in capsule form. Where a given batch of coated spheroids releases drug too slowly to comply with the desired dissolution rate study, a portion of uncoated spheroids or spheroids with a lower coating level may be added to the batch to provide, after thorough mixing, a loading dose for rapid increase of blood drug levels. A batch of coated spheroids that releases the drug too rapidly can receive additional film-coating to give the desired dissolution profile.

TABLE 1

Acceptable Coated Spheroid Dissolution Rates

| Time (hours) | Average % Venlafaxine HCl released |
| --- | --- |
| 2 | <30 |
| 4 | 30–55 |
| 8 | 55–80 |
| 12 | 65–90 |
| 24 | >80 |

Batches of the coated venlafaxine hydrochloride containing spheroids which have a dissolution rate corresponding to that of Table 1 are filled into pharmaceutically acceptable capsules in an amount needed to provide the unit dosage level desired. The standard unit dosage immediate release (IR) tablet used presently provides amounts of venlafaxine hydrochloride equivalent to 25 mg, 37.5 mg, 50 mg, 75 mg and 100 mg venlafaxine. The capsules of this invention are filled to provide an amount of venlafaxine hydrochloride equivalent to that presently used in tablet form and also up to about 150 mg venlafaxine hydrochloride.

Dissolution of the venlafaxine hydrochloride ER capsules is determined as directed in the U. S. Pharmacopoeia (USP) using apparatus 1 at 100 rpm on 0.9 L of water. A filtered sample of the dissolution medium is taken at the times specified. The absorbance of the clear solution is determined from 240 to 450 nanometers (nm) against the dissolution medium. A baseline is drawn from 450 nm through 400 nm and extended to 240 nm. The absorbance at the wavelength of maximum absorbance (about 274 nm) is determined with respect to this baseline. Six hard gelatin capsules are filled with the theoretical amount of venlafaxine hydrochloride spheroids and measured for dissolution. Standard samples consist of venlafaxine hydrochloride standard solutions plus a gelatin capsule correction solution.

The percentage of venlafaxine released is determined from the equation $$\% \text{ Venlafaxine hydrochloride released} = \frac{(As)(Wr)(S)(V1)(0.888)(100)}{(Ar)(V2)(C)}$$

where As is absorbance of sample preparation, Wr is weight of reference standard, mg; S is strength of the reference standard, decimal; V1 is the volume of dissolution medium used to dissolve the dosage form, mL; 0.884 is the percent free base, Ar is the absorbance of the standard preparation, V2 is the volume of reference standard solution, mL; and C is the capsule claim in mg.

Table 2 shows the plasma level of venlafaxine versus time for one 75 mg conventional Immediate Release (IR) tablet administered every 12 hours, two 75 mg extended release (ER) capsules administered simultaneously every 24 hours, and one 150 mg extended release (ER) capsule administered once every 24 hours in human male subjects. The subjects were already receiving venlafaxine hydrochloride according to the dosage protocol, thus the plasma blood level at zero time when dosages were administered is not zero.

TABLE 2

Plasma venlafaxine level (ng/mL) versus time, conventional tablet (not extended release) versus ER capsule

| Time (hours) | 75 mg (IR)tablet (q 12 h) | 2 × 75 mg (ER)capsules (q 24 hr) | 1 × 150 mg (ER)capsules (q 24 h) |
|---|---|---|---|
| 0 | 62.3 | 55.0 | 55.8 |
| 0.5 | 76.3 | | |
| 1 | 135.6 | 53.3 | 53.2 |
| 2 | 212.1 | 69.8 | 70.9 |
| 4 | 162.0 | 138.6 | 133.3 |
| 6 | 114.6 | 149.0 | 143.5 |
| 8 | 86.7 | 129.3 | 129.5 |
| 10 | | 118.4 | 114.4 |
| 12 | 51.9 | 105.1 | 105.8 |
| 12.5 | 74.7 | | |
| 13 | 127.5 | | |
| 14 | 161.3 | 90.5 | 91.3 |
| 16 | 134.6 | 78.2 | 78.5 |
| 18 | 106.2 | | |

TABLE 2-continued

Plasma venlafaxine level (ng/mL) versus time, conventional tablet (not extended release) versus ER capsule

| Time (hours) | 75 mg (IR)tablet (q 12 h) | 2 × 75 mg (ER)capsules (q 24 hr) | 1 × 150 mg (ER)capsules (q 24 h) |
|---|---|---|---|
| 20 | 83.6 | 62.7 | 63.3 |
| 24 | 57.6 | 56.0 | 57.3 |

Table 2 shows that the plasma levels of two 75 mg/capsule venlafaxine hydrochloride ER capsules and one 150 mg/capsule venlafaxine hydrochloride ER capsule provide very similar blood levels. The data also show that the plasma level after 24 hours for either extended release regimen is very similar to that provided by two immediate release 75 mg tablets of venlafaxine hydrochloride administered at 12 hours intervals.

Further, the plasma levels of venlafaxine obtained with the extended release formulation do not increase to the peak levels obtained with the conventional immediate release tablets given 12 hours apart. The peak level of venlafaxine from (ER), somewhat below 150 ng/ml, is reached in about six hours, plus or minus two hours, based upon this specific dose when administered to patients presently under treatment with venlafaxine hydrochloride (IR). The peak plasma level of venlafaxine, somewhat over 200 ng/ml, following administration of (IR) is reached in two hours and falls rapidly thereafter.

Table 3 shows venlafaxine blood plasma levels in male human subjects having a zero initial blood plasma level. Again, a peak blood plasma concentration of venlafaxine is seen at about 6 hours after dosing with venlafaxine hydrochloride extended release capsules in the quantities indicated. The subjects receiving the single 50 mg immediate release tablet showed a peak plasma level occurring at about 4. hours. For comparative purposes, the plasma levels of venlafaxine for subjects receiving the conventional formulated tablet can be multiplied by a factor of three to approximate the plasma levels expected for a single dose of 150 mg. conventional formulation.

TABLE 3

Plasma Blood Levels in Human Males Having No Prior Venlafaxine Blood Level

| Time (Hours) | 1 × 50 mg IR tablet | 2 × 75 mg ER capsules | 1 × 150 mg ER capsule |
|---|---|---|---|
| 0 | 0 | 0 | 0 |
| 1 | 27.87 | 1.3 | 0 |
| 1.5 | 44.12 | 6.0 | 2.2 |
| 2 | 54.83 | 20.6 | 12.8 |
| 4 | 66.38 | 77.0 | 81.0 |
| 6 | 49.36 | 96.5 | 94.4 |
| 8 | 30.06 | 93.3 | 86.9 |
| 10 | 21.84 | 73.2 | 72.8 |
| 12 | 15.91 | 61.3 | 61.4 |
| 14 | 13.73 | 52.9 | 51.9 |
| 16 | 10.67 | 47.5 | 41.1 |
| 20 | 5.52 | 35.2 | 34.0 |
| 24 | 3.56 | 29.3 | 28.5 |
| 28 | 2.53 | 23.4 | 22.9 |
| 36 | 1.44 | 11.9 | 13.5 |
| 48 | 0.66 | 5.8 | 5.2 |

The blood plasma levels of venlafaxine were measured according to the following procedure. Blood samples from the subjects were collected in heparinized evacuated blood tubes and the tubes were inverted gently several times. As quickly as possible, the tubes were centrifuged at 2500 rpm for 15 minutes. The plasma was pipetted into plastic tubes and stored at −20° C. until analysis could be completed.

To 1 mL of each plasma sample in a plastic tube was added 150 μL of a stock internal standard solution (150 μg/ml). Saturated sodium borate (0.2 mL) solution was added to each tube and vortexed. Five mL of ethyl ether was added to each tube which were then capped and shaken for 10 minutes at high speed. The tubes were centrifuged at 3000 rpm for 5 minutes. The aqueous layer was frozen in dry ice and the organic layer transferred to a clean screw cap tube. A 0.3 mL portion of 0.01 N HCl solution was added to each tube and shaken for 10 minutes at high speed. The aqueous layer was frozen and the organic layer removed and discarded. A 50 μL portion of the mobile phase (23:77 acetonitrile:0.1M monobasic ammonium phosphate buffer, pH 4.4) was added to each tube, vortexed, and 50 μL samples were injected on a Supelco Supelcoil LC-8-DB, 5 cm×4.6 mm, 5 μ; column in a high pressure liquid chromatography apparatus equipped with a Waters Lambda Max 481 detector or equivalent at 229 nm. Solutions of venlafaxine hydrochloride at various concentrations were used as standards.

EXAMPLE NO. 5

Manufactured by the techniques described herein, another preferred formulation of this invention comprises spheroids of from about 30% to about 35% venlafaxine hydrochloride and from about 0.3% to about 0.6% hydroxypropylmethylcellulose. These spheroids are then coated with a film coating, as described above, to a coating level of from about 5% to about 9%, preferably from about 6% to about 8%. A specific formulation of this type comprises spheroids of about 33% venlafaxine hydrochloride and about 0.5% hydroxypropylmethylcellulose, with a film coating of about 7%.

Lower dosage compositions or formulations of this invention may also be produced by the techniques described herein. These lower dosage forms may be administered alone for initial titration or initiation of treatment, prior to a dosage increase. They may also be used for an overall low-dose administration regimen or in combination with higher dosage compositions, such as capsule formulations, to optimize individual dosage regimens.

These lower dose compositions may be used to create encapsulated formulations, such as those containing doses of venlafaxine hydrochloride from about 5 mg to about 50 mg per capsule. Particular final encapsulated dosage forms may include, but are not limited to, individual doses of 7.5 mg, 12.5 mg, 18.75 mg, or 28.125 mg of venlafaxine HCl per capsule.

The spheroids useful in these lower dose formulations may comprise from about 5% to about 29.99% venlafaxine HCl, preferably from about 5% to about 25%, from about 75% to about 95% microcrystalline cellulose, and, optionally from about 0.25% to about 1.0% hydroxypropylmethylcellulose. The spheroids may be coated as described above, preferably with a film coating of from about 5% to about 10% by is weight. In some preferred formulations, the spheroids comprise the cited venlafaxine HCl and microcrystalline cellulose, with no hydroxypropylmethyl cellulose.

EXAMPLE NO. 6

Spheroids comprising 16.5% venlafaxine HCl and 83.5% microcrystalline cellulose were mixed with approximately 50% water (w/w) to granulate in a Littleford Blender Model FM-50E/1Z (Littleford Day Inc., P.O. Box 128, Florence, Ky. 41022-0218, U.S.A.) at a fixed speed of 180 rpm. The blended material was extruded through a 1.25 mm screen using a Nica extruder/speronization machine (Aeromatic-Fielder Division, Niro Inc., 9165 Rumsey Rd., Columbia, Md. 21045, U.S.A.) for a 12/20 mesh cut after drying. Two portions of the resulting spheroids were coated with a 5% and 7% coating level, respectively, by techniques described above using the coating formulation:

| Ingredient | % (w/w) |
|---|---|
| Methylene Chloride | 60.000 |
| Methanol Anhydrous | 35.500 |
| Ethylcellulose, NF, HG 2834, 50 cps | 3.825 |
| Hydroxypropyl Methylcellulose, 2910 USP, 6 cps | 0.675 |

These 5% and 7% coated lots were tested for dissolution on a Hewlett Packard automated dissolution system over a 24 hour period, resulting in the following dissolution patterns

| Time/hr | % Dissoluded 16.5%/5% | % Dissolved 16.5%/7% |
|---|---|---|
| 2 | 12.4 | 5.6 |
| 4 | 42.8 | 25.4 |
| 8 | 70.7 | 60.4 |
| 12 | 82.2 | 75.4 |
| 24 | 94.3 | 92.7 |

EXAMPLE NO. 7

A formulation of spheroids containing 8.25% venlafaxine HCl and 91.75% microcellulose was prepared according to the techniques of Example No. 6 and coated with a 5% film coating. In the Hewlett Packard automated dissolution system these spheroids provided the following dissolution profile:

| Time/hr | % Dissolved 8.25%/5% |
|---|---|
| 2 | 4.4 |
| 4 | 24.2 |
| 8 | 62.9 |
| 12 | 77.8 |
| 24 | 93.5 |

Thus, the desired dissolution rates of sustained release dosage forms of venlafaxine hydrochloride, impossible to achieve with hydrogel tablet technology, has been achieved with the film-coated spheroid compositions of this invention.

What is claimed is:

1. An extended release formulation of venlafaxine hydrochloride comprising a pharmaceutically acceptable capsule containing spheroids comprised of from about 6% to about 40% venlafaxine hydrochloride by weight, about 50% to about 94% microcrystalline cellulose, NF, by weight, and optionally from about 0.25% to about 1% by weight of hydroxypropyl-methylcellulose, USP, wherein the spheroids are coated with a film coating composition comprised of ethyl cellulose and hydroxypropylmethylcellulose.

2. An extended release formulation of venlafaxine hydrochloride according to claim 1 which provides peak serum levels of up to 150 ng/ml and extended therapeutically effective plasma levels over a twenty four hour period.

3. An extended release formulation according to claim 1 wherein the spheroids are coated with from about 2% to about 12% of total formulation weight of film coating comprised of from about 80% to about 90% by weight of film coating of ethyl cellulose, NF, and from about 10% to about 20% by weight of film coating of hydroxypropylmethylcellulose, USP.

4. An extended release formulation according to claim 1 wherein the spheroids are comprised of from about 30% to 40% venlafaxine hydrochloride by weight, about 50% to about 70% microcrystalline cellulose, NF, by weight, and, optionally, from about 0.25% to about 1% by weight of hydroxypropylmethylcellulose, USP.

5. An extended release formulation according to claim 4 wherein the spheroids are coated with from about 2% to about 12% of total formulation weight of film coating comprised of from about 80% to about 90% by weight of film coating of ethyl cellulose, NF, and from about 10% to about 20% by weight of film coating of hydroxypropylmethylcellulose, USP.

6. An extended release formulation according to claim 1 wherein the spheroids comprise from about 6% to about 30% venlafaxine hydrochloride by weight, about 70.1% to about 94% microcrystalline cellulose, NF, by weight and, optionally, from about 0.25% to about 1% by weight of hydroxypropylmethylcellulose.

7. An extended release formulation according to claim 6 wherein the spheroids are coated with from about 2% to about 12% of total weight of film coating comprised of from about 80% to about 90% by weight of film coating of ethyl cellulose, NF, and from about 10% to about 20% by weight of film coating of hydroxypropylmethylcellulose, USP.

8. An extended release formulation according to claim 1 wherein the spheroids comprise from about 5% to about 25% venlafaxine hydrochloride and from about 95% to about 75% microcrystalline cellulose, with an optional amount of from 0.25% to about 1% by weight of hydroxypropylmethylcellulose.

9. An extended release formulation according to claim 6 wherein the spheroids comprise from about 6% to about 25% venlafaxine hydrochloride and from about 94% to about 75% microcrystalline cellulose, with an optional amount of from 0.25% to about 1% by weight of hydroxypropylmethylcellulose.

10. An extended release formulation according to claim 6 wherein the spheroids comprise from about 6% to about 20% venlafaxine hydrochloride and from about 94% to about 80% microcrystalline cellulose, with an optional amount of from 0.25% to about 1% by weight of hydroxypropylmethylcellulose.

11. An encapsulated, extended release formulation of venlafaxine hydrochloride according to claim 1 having the following dissolution profile in USP Apparatus 1 (basket) at 100 rpm in purified water at 37° C:

| Time (hours) | Average % Venlafaxine HCl released |
| --- | --- |
| 2 | <30 |
| 4 | 30–55 |
| 8 | 55–80 |
| 12 | 65–90 |
| 24 | >80 |

12. An extended release formulation according to claim 1 wherein the spheroids are composed of about 37% by weight of venlafaxine hydrochloride, about 0.5% by weight of hydroxypropylmethylcellulose, and about 62% by weight of microcrystalline cellulose.

13. An extended release formulation according to claim 1 wherein the film coating is comprised of ethyl cellulose (4.81% of total weight) and hydroxypropylmethylcellulose (0.85% of total weight).

14. An extended release formulation according to claim 1 wherein the film coating comprises 6–8% by weight of total weight.

15. An extended release formulation according to claim 1 wherein the film coating is comprised of ethyl cellulose (2.48% of total weight) and hydroxypropylmethylcellulose (0.437% of total weight).

16. An extended release formulation according to claim 1 wherein the film coating composition is comprised of ethyl cellulose having a 44.0–51.0% content of ethoxy groups and hydroxypropylmethylcellulose having a methoxy content of 28.0–30.0% and a hydroxypropoxy group content of 7.0–12.0%.

17. An extended release formulation according to claim 1 wherein the film coating composition is comprised of about 85% by total weight of film coating of ethyl cellulose having 44.0–51% content of ethoxy groups and about 15% by total weight of film coating of hydroxypropylmethylcellulose having a methoxy content of 28.0–30.0% and a hydroxypropoxy group content of 7.0–12.0%.

18. An extended release formulation according to claim 1 wherein the film coating composition is comprised of 85% by weight of ethyl cellulose having an ethoxy content of 44.0–51% and a viscosity of 50% cps for a 5% aqueous solution, and 15% by weight of hydroxypropylmethylcellulose having a viscosity of 6 cps at 2% aqueous solution with a methoxy content of 28–30% and a hydroxypropoxy content of 7–12%.

19. An extended release formulation of venlafaxine hydrochloride for once daily administration which comprises spheroids containing 37.3% venlafaxine, 62.17% microcrystalline cellulose and 0.5% hydroxypropylmethylcellulose coated with a quantity of a mixture comprised of 85% ethyl cellulose and 15% hydroxypropylmethylcellulose sufficient to give coated spheroids having a dissolution profile in USP Apparatus 1 (basket) at 100 rpm in purified water at 37° C.:

| Time | Average % Venlafaxine HCl Released |
| --- | --- |
| 2 | <30 |
| 4 | 30–55 |
| 8 | 55–80 |
| 12 | 65–90 |
| 24 | >80. |

20. A method for providing a therapeutic blood plasma concentration of venlafaxine over a twenty four hour period with diminished incidences of nausea and emesis which comprises administering orally to a patient in need thereof, an encapsulated, extended release formulation that provides a peak blood plasma level of venlafaxine in from about four to about eight hours, said formulation containing venlafaxine hydrochloride as the active ingredient.

21. A method for eliminating the troughs and peaks of drug concentration in a patients blood plasma attending the therapeutic metabolism of plural daily doses of venlafaxine hydrochloride which comprises administering orally to a patient in need thereof, an encapsulated, extended release formulation that provides a peak blood plasma level of venlafaxine in from about four to about eight hours, said formulation containing venlafaxine hydrochloride as the active ingredient.

22. A method for providing a therapeutic blood plasma concentration of venlafaxine over a twenty-four hour period with diminished incidence of nausea and emesis which comprises administering orally to a patient in need thereof, an encapsulated extended release formulation that provides a peak blood plasma level of venlafaxine in from about 5 to about 8 hours, said formulation containing venlafaxine hydrochloride as the active ingredient.

23. A method for providing a therapeutic blood plasma concentration of venlafaxine over a twenty-four hour period with diminished incidence of nausea and emesis which comprises administering orally to a patient in need thereof, an encapsulated extended release formulation that provides a peak blood plasma level of venlafaxine in about 6 hours, said formulation containing venlafaxine hydrochloride as the active ingredient.

24. A method for eliminating the troughs and peaks of drug concentration in a patient's blood plasma attending the therapeutic metabolism of plural daily doses of venlafaxine hydrochloride which comprises administering orally to a patient in need thereof, an encapsulated, extended release formulation that provides a peak blood plasma level of venlafaxine in from about 5 to about 8 hours, said formulation containing venlafaxine hydrochloride as the active ingredient.

25. A method for eliminating the troughs and peaks of drug concentration in a patient's blood plasma attending the therapeutic metabolism of plural daily doses of venlafaxine hydrochloride which comprises administering orally to a patient in need thereof, an encapsulated, extended release formulation that provides a peak blood plasma level of venlafaxine in about 6 hours, said formulation containing venlafaxine hydrochloride as the active ingredient.

* * * * *